Oct. 14, 1958 H. SACHSSE ET AL Re. 24,550

PROCESS FOR THE PRODUCTION OF ACETYLENE BY INCOMPLETE COMBUSTION OF HYDROCARBONS

Original Filed May 18, 1950

INVENTORS:
HANS SACHSSE
THOMAS KOSBAHN
ERWIN LEHRER

BY Marzall, Johnston, Cook & Root

ATT'YS

United States Patent Office

Re. 24,550
Reissued Oct. 14, 1958

24,550

PROCESS FOR THE PRODUCTION OF ACETYLENE BY INCOMPLETE COMBUSTION OF HYDROCARBONS

Hans Sachsse, Wiesbaden, Thomas Kosbahn, Mannheim-Friedrichsfeld, and Erwin Lehrer, Bad Duerkheim, Germany, assignors to Badische Anilin- & Soda-Fabrik Aktiengesellschaft, Ludwigshafen am Rhein, Germany Original No. 2,664,450, dated December 29, 1953, Serial No. 162,685, May 18, 1950. Application for reissue March 5, 1958, Serial No. 723,621

4 Claims. (Cl. 260—679)

Figure 1:
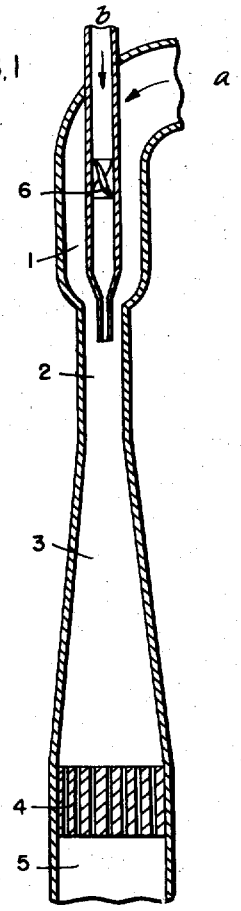

Matter enclosed in heavy brackets [ ] appears in the original patent but forms no part of this reissue specification; matter printed in italics indicates the additions made by reissue.

The present invention relates to the production of acetylene by incomplete combustion of hydrocarbons and the object of this invention is an improved process suitable for carrying out the said acetylene producing method.

The preferred technique in producing acetylene by incomplete combustion of hydrocarbons with oxygen is to preheat the hydrocarbons and the oxygen separately and to subject them, after mixing, to reaction with the formation of a flame, care being taken that the flame reaction does not encroach into the mixing chamber for the gases, because by the striking back of the very hot flame, the apparatus would be injured or destroyed. Since the gases, by reason of the preheating, are in a reactive condition, it is furthermore necessary to effect the intimate mixing of the gases in the shortest possible time so that the possibility of a premature reaction in the mixing chamber is minimized. Whereas quite a number of techniques are known to satisfy these demands in small-scale operations, substantial difficulties are encountered when operating in larger scale. In this case it has been proposed to split up the amount of oxygen to be mixed with the hydrocarbons into several partial streams and to do the mixing by means of nozzles arranged parallel to each other, or to cause the two gases to flow together through slits, series of holes or channels or to allow them to impinge on each other at high speeds, and to keep the chamber adjoining the place at which mixing takes place and through which the gas mixture has to flow to the point where the flame reaction takes place as small as possible in order to avoid too long and injurious a sojourn of the preheated, very reactive mixture therein. Furthermore, it has been found convenient to adopt the space between the mixing means and the flame chamber to the size and shape of the flame chamber, to improve operation.

It has been found, however, that such apparatus, while providing a substantial improvement, do not satisfy the requirements when large amounts of hydrocarbons are to be handled in a continuous process; for example, when throughputs of 1000 cubic meters of hydrocarbons or more per hour are contemplated. The gas mixture will then, even in these apparatus, be liable to premature reactions and back-flashing of the flame which even accurate supervision can scarcely avoid, so that frequent interruption of the operation and destruction of the burners result.

The object of this invention is a combustion process for the production of acetylene by incomplete combustion of hydrocarbons which substantially comprises using a supply means for the gases to be reacted, this means being arranged in as symmetrical as posisble a position about the axis of the direction of flow of the gas mixture, an elongated mixing chamber of, preferably, circular cross-section following the supply means and a gas distributor preceding the flame chamber. The symmetrical shape of the supply means and the elongated shape of the mixing chamber make the two gases entering in a preheated state meet each other with practically the same direction of flow, and slow down by degrees the speed of the gas mixture in the long narrow space, serving to complete the mixing, so that no eddies are formed such as would give rise to detrimental retardation of the outlet from the mixing chamber. The length of the mixing chamber should be at least three times its width. A preferred form of construction provides enlarging the mixing chamber conically towards the gas distributor and giving it a very slight opening angle.

The speed of flow of the two gases at their junction point is chosen high enough so that a flame cannot live therein. For this purpose the sum of the mean speeds of the hydrocarbon gas and the oxygen gas should be greater than about 70 meters per second, measured at 0° C. and 760 millimeters (mercury gauge).

Various embodiments of apparatus used according to the invention are shown in the accompanying drawings but the invention is not limited to the particular embodiments shown.

Referring to the drawings, Figs. 1, 2, 3a and 3b represent elevations, at least partly in section, of various forms of apparatus suitable for use according to the invention.

Referring to Figure 1, the gas supply tube a and the smaller-sized tube b for the supply of the other gas are concentrically fitted into one another so as to form the nozzle 1. This merges into a mixing tube 2 and then into a conical mixing chamber 3 which is separated from the reaction or flame chamber 5 proper by a gas distributor 4 consisting of numerous parallel tubes or of a block provided with numerous channels. For a rapid mixing of the gases it is useful to impart to one of the gas streams a spiral movement, for example, by providing whirling means 6 in tube b.

Figure 2:
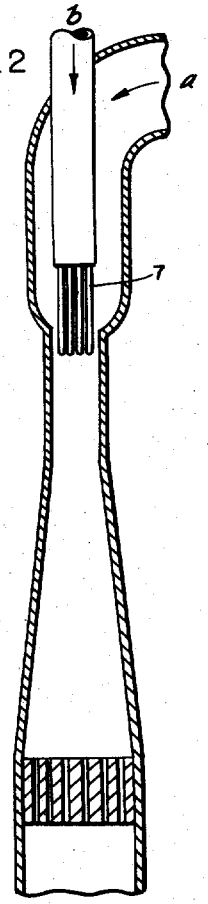

Referring to Figure 2, this shows a modification of the apparatus shown in Figure 1 in which the tube b terminates in a bundle of narrow tubes 7.

Figure 3A:
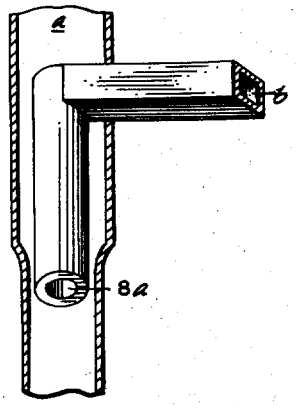
Figure 3B:
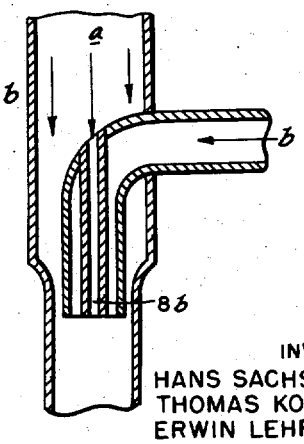

According to the modification shown in Figures 3a and 3b, a sort of annular nozzle 8a or 8b is provided by which the gas stream entering through the tube a is split up into two parts, so that one of the partial streams meets the gas stream-introduced through the tube b in its axis part while the other meets it at its periphery.

Employing the combustion process of the invention, it is possible to work up, safely and without trouble, considerably larger amounts of hydrocarbons into gas mixtures containing acetylene than hitherto.

The following example will further illustrate this invention but the invention is not limited to this example.

EXAMPLE 1000 cubic meters of methane and 600 cubic meters of oxygen per hour are introduced into one of the apparatus shown in the drawings. The methane enters through the tube a and the oxygen through the tube b. Both gases are heated to from 500° to 600° C. before entry. The gas mixture leaving the flame chamber 5 contains, in addition to 8.8 percent of acetylene, 6.4 percent of methane, 0.2 percent of ethylene, 24.6 percent of carbon monoxide, 3.4 percent of carbon dioxide, 56.2 percent of hydrogen and 0.4 percent of oxygen.

What we claim is:

1. A process for the production of acetylene by incomplete combustion of preheated hydrocarbon gas with oxygen which comprises supplying the hydrocarbon gas through a tube concentrically located [within] *around* another tube through which the oxygen is supplied, mixing the two gases in an elongated chamber of circular cross-section adjacent to said supply tubes and adapted to receive said gases, and distributing the gas mixture prior to its entry into the combustion chamber by means of a block having a plurality of parallel channels therethrough, the cross-sectional area of said mixing chamber increasing from the end of said supply tubes to the end of said distributor block and the length of said mixing chamber being at least three times its width.

2. A process for the production of acetylene by incomplete combustion of preheated hydrocarbon gas with oxygen which comprises supplying the hydrocarbon gas through a tube concentrically located [within] *around* another tube through which the oxygen is supplied, while maintaining such a speed of flow of the two gases at their junction point that the sum of their mean speeds exceeds 70 meters per second, measured at 0° C. and 760 millimetres (mercury gauge), mixing the two gases in an elongated chamber of circular cross-section adjacent to said supply tubes and adapted to receive said gases, and distributing the gas mixture prior to its entry into the combustion chamber by means of a block having a plurality of parallel channels therethrough, the cross-sectional area of said mixing chamber increasing from the end of said supply tubes to the end of said distributor block and the length of said mixing chamber being at least three times its width.

3. A process for the production of acetylene by incomplete combustion of preheated methane gas with oxygen which comprises supplying the methane gas through a tube concentrically located [within] *around* another tube through which the oxygen is supplied, mixing the two gases in an elongated chamber of circular cross-section adjacent to said supply tubes and adapted to receive said gases, and distributing the gas mixture prior to its entry into the combustion chamber by means of a block having a plurality of parallel channels therethrough, the cross-sectional area of said mixing chamber increasing from the end of said supply tubes to the end of said distributor block and the length of said mixing chamber being at least three times its width.

4. A process for the production of acetylene by incomplete combustion of preheated methane gas with oxygen which comprises supplying the methane gas through a tube concentrically located [within] *around* another tube through which the oxygen is supplied, while maintaining such a speed of flow of the two gases at their junction point that the sum of their mean speeds exceeds 70 metres per second, measured at 0° C. and 760 millimetres (mercury gauge), mixing the two gases in an elongated chamber of circular cross-section adjacent to said supply tubes and adapted to receive said gases, and distributing the gas mixture prior to its entry into the combustion chamber by means of a block having a plurality of parallel channels therethrough, the cross-sectional area of said mixing chamber increasing from the end of said supply tubes to the end of said distributor block and the length of said mixing chamber being at least three times its width.

References Cited in the file of this patent or the original patent

UNITED STATES PATENTS

| | | |
|---|---|---|
| 238,852 | Church | Mar. 15, 1881 |
| 246,321 | Litchfield et al. | Aug. 30, 1881 |
| 329,776 | Robertson et al. | Nov. 3, 1885 |
| 889,701 | Luckenbach | June 2, 1908 |
| 2,552,277 | Hasche | May 8, 1951 |